US006864983B2

(12) United States Patent
Galle et al.

(10) Patent No.: US 6,864,983 B2
(45) Date of Patent: Mar. 8, 2005

(54) METHOD FOR MEASURING OF GASEOUS EMISSIONS AND/OR FLUX

(76) Inventors: Bo Galle, Dunasen, Nossebro (SE), SE-465 93; Johan Mellqvist, Bredmossegatan 1D, Goteborg (SE), SE-416 74

(*) Notice: Subject to any disclaimer, the term of this patent is extended or adjusted under 35 U.S.C. 154(b) by 99 days.

(21) Appl. No.: 10/332,812
(22) PCT Filed: Jul. 9, 2001
(86) PCT No.: PCT/SE01/01583
§ 371 (c)(1), (2), (4) Date: Jan. 13, 2003
(87) PCT Pub. No.: WO02/04902
PCT Pub. Date: Jan. 17, 2002

(65) Prior Publication Data
US 2004/0012787 A1 Jan. 22, 2004

(30) Foreign Application Priority Data
Jul. 12, 2000 (SE) .............................. 0002625

(51) Int. Cl.$^7$ ............................................. G01N 21/61
(52) U.S. Cl. .................................... 356/437; 250/338.5
(58) Field of Search ................................. 356/437, 438; 250/338.5, 343.2

(56) References Cited
U.S. PATENT DOCUMENTS 3,849,005 A * 11/1974 Girard et al. ............... 356/438
3,868,186 A * 2/1975 Paukert et al. .............. 356/438
4,605,313 A * 8/1986 Kebabian ..................... 374/121
5,391,883 A * 2/1995 Kinsey et al. ............... 250/372

OTHER PUBLICATIONS

C. Paton Walsh et al., "An Uncertainty Budget for Ground-Based Fourier Transform Infrared Column Measurements of HCl, HF, $N_2O$, and $HNO_3$ Deduced from Results of Side-By-Side Instrument Intercomparisons," Journal of Geophysical Research, V. 102, 1997, pp. 8867–8873.

* cited by examiner

Primary Examiner—Richard A. Rosenberger
(74) Attorney, Agent, or Firm—Young & Thompson

(57) ABSTRACT

Method for measuring gaseous emissions and/or flux based on using a spectrometer instrument for receiving absorption spectra to detect and record, in a wavelength-resolved manner, the electromagnetic radiation which is coming directly from the sun. The instrument is arranged in such a way that the connecting line between the instrument and the sun transects a gas volume which constitutes all or part of the gas flow emitted from a source. The electromagnetic radiation which is recorded is used for calculating the gas concentration along the optical connecting line in the gas volume. The concentration which is obtained in this way, and which is integrated over the cross-sectional area traversed by the connecting line, is used, together with information on the speeds of the wind, the instrument and the gas-emitting source, to calculate the gas flow through the cross-sectional area which is traversed.

10 Claims, 2 Drawing Sheets

METHOD FOR MEASURING OF GASEOUS EMISSIONS AND/OR FLUX

INTRODUCTION

Method for measuring gaseous emissions and/or flux based on the eleclromagnetic radiation coming directly from the sun being detected and recorded, in a wavelength-resolved manner, using a spectrometric instrument for receiving absorption spectra.

BACKGROUND

Nowadays, mankind's activities affect our environment on a local, regional and global scale. This has led to serious environmental disturbances. Examples related to our atmosphere are concentrations of air pollutants in urban air and industrial areas which are injurious to heath, the regional formation of ozone and the destruction of trees by pollution, and global effects on the climate and the protective ozone layer in the stratosphere. In order to understand the mechanisms behind these problems and to be able to take cost-effective action, there is a requirement for measurements of the gas emissions which are the cause of the problems which have arisen. In some cases, these emissions are well-demarcated locally, for example discharges through chimneys and vents, and the emissions can be measured by measuring the concentration and gas flow at the source. In many cases, however, the emission source is "diffuse", i.e. dispersed over a relatively large area. Examples of this are the emission of hydrocarbons from petrochemical plants or a refinery, the emission of methane from a refuse disposal site or the emission of nitrogen oxides from a town. Quantifying the emission from this type of source constitutes a substantially greater measurement challenge from the technical point of view. Five different measurement strategies which are nowadays used for quantifying diffuse gaseous emissions are described in the following section.

1. Meteorological Method:

In this method, the concentration of the gas in question is measured at one or several points at a suitable distance from the source. By means of using a meteorological dispersion model, the dispersion of the gas can be modelled and the strength of the source can be calculated. The method depends entirely on the reliability of the meteorological model and can therefore only be used when the topography and the meteorology are suitable. An example is the measurement of emissions such as carbon dioxide and methane from arable land (flat terrain, no buildings or trees allowed to disturb the wind field within 200–500 m). When industrial emissions are being measured, the method is quite unsuitable due to the effect of the buildings on the wind field, hot discharges, etc.

2. The Tracer Gas Method:

This can be said to be a variant of the above-mentioned method. In this case, too, the concentration of the gas under study is measured at one or several points on the lee side of the source. Instead of calculating the dispersal using a meteorological model, this is done empirically by releasing a tracer gas of known emission at the source. The concentration of the tracer gas is then measured at the same time as the gas under study is measured. In this connection, it is possible to determine the relationship between the concentration and emission in the case of the tracer gas. If the tracer gas has the same physical properties (temperature and density) as the gas under study, this relationship can then also be used for determining the emission of the gas under study. The method presupposes that the two gases are mixed well, something which in turn presupposes suitable meteorological conditions and that the tracer gas is released in a manner which simulates well the emission of the gas under study.

3. Line Integration:

Both the above-mentioned methods suffer from the weakness that the measurements are only made at one or several points in the air mass which is emitted. The reliability of the determinations can be substantially improved by using line integration to make the concentration measurements. This can be achieved by using line-integrating optical methods such as DOAS (differential optical absorption spectroscopy) or LPFTIR (long-path Fourier transform infrared spectroscopy), what is termed "cross-wind integration". In this connection, electromagnetic radiation is transmitted over a distance which transects the air mass in question and absorption spectroscopy can be used to determine the mean concentration over the measurement distance in question, after which the emission is determined using one of the above-mentioned methods.

4. Laser Radar:

Additional reliability in the determination can be obtained if the gas concentration is integrated over the whole of the cross section of the emitted gas mass on the lee side of the source. A method which does this is DIAL (differential absorption lidar). This method is used to emit laser light of different wavelengths in a well-defined direction. By means of the time-resolved detection of the light which is back-scattered from particles and molecules, it is possible to obtain a distance-resolved determination of the gas concentration along the laser beam. By measuring sequentially in different directions using different elevations, it is possible to obtain the integrated concentration over a cross section of the whole of the emitted gas mass. If the cross section is placed perpendicular to the wind, the total emission can then be obtained if the concentration is multiplied by the concentration-weighted wind speed. The strength of the method is that the whole of the emitted gas mass is integrated and that it is not necessary to use a meteorological dispersal model. The uncertainty in the measurements is largely determined by the uncertainty in determining the wind field. The disadvantages of the method are that only a few gases can be measured and that the measuring equipment is expensive and complicated and requires qualified personnel, thereby making the measurements expensive.

5. Sky-light Spectroscopy:

Integrating sky-light spectroscopy is an alternative method which also integrates over the whole of the cross section of the emitted air mass. This method uses a spectrometer to record the light of the zenithal sky. This results in a spectrum of the zenithal sky including the vertically integrated concentration of the gases which are present in the atmosphere. By means of moving the spectrometer in such a way that the vertical stretch which is measured cuts the emitted gas mass, it is possible, after subtracting the contribution made by the background concentration, to determine the integrated concentration over a cross section of the emitted gas mass. The emission is obtained after multiplying by the concentration-weighted wind speed transversely to the direction of traversal. While the method uses relatively simple equipment, it is limited to a small number of molecules which can be measured in the 300–700 nm range of the electromagnetic spectrum, i.e. the spectral range within which the zenithal sky scatters sunlight. In addition, the measurements are affected by variable multiple scattering, for example in clouds, and by what is termed the Ring effect (partial filling-in of the Fraunhofer lines in the solar spectrum caused by Raman scattering). The method has therefore principally been used for measuring industrial emissions of $SO_2$ and $NO_2$ and for quantifying emissions of $SO_2$ from volcanoes.

ACCOUNT OF THE INVENTION

The object of the present invention is, by means of elaborating the above-discussed methods, to produce a measurement method which offers a unique and cost-effective method for measuring emissions and flux of gaseous substances both from industries and from other anthropogenic and natural sources.

The said object is achieved by means of the method according to the present invention, which method is characterized in that the instrument is arranged in such a way that the connecting line between the instrument and the sun transects a gas volume which constitutes all or part of the gas flow emitted from a source, in that the electromagnetic radiation which is recorded is used for calculating the gas concentration along the optical connecting line in the gas volume, and in that the concentration which is thus obtained, and which is integrated over the cross-sectional area which is traversed by the connecting line, is used, together with information about the speeds of the wind, the instrument and the gas-emitting source, to calculate the gas flow through the traversed cross-sectional area.

The method is based on solar spectroscopy and involves a spectrometer being coupled to what is termed a sun tracker, i.e. a mirror system which "locks" onto the sun in such a way that the direct sunlight always impinges on the entry aperture of the spectrometer. The instrument thus records spectra of the sun as seen through the atmosphere. By means of evaluating the absorption spectra which are obtained, it is then possible to determine the integrated total column of the gas in question along the optical path between the instrument and the sun. The optical path is understood as meaning the route which the sunlight has taken/passed along between the sun and the instrument. When the sun is low in the sky, this path differs from the geometrical connecting line because of the refraction of the sunlight in the atmosphere. By means of either placing or moving the instrument in such a way that the line between the instrument and the sun transects the air mass on the lee side of the source whose emission it is desired to quantify, it is possible to determine the integrated concentration, expressed in mass per unit length, e.g. $g \cdot m^{-1}$, over a cross section of the air mass after the background concentration has been subtracted. If this value is then multiplied by the wind speed in the plume transversely to the direction of traversal, the emission can then be obtained expressed in mass per unit of time, e.g. $g \cdot s^{-1}$.

Flux is understood as meaning the transport of gas through what is normally a vertical cross-sectional area expressed in mass per unit of time and area, for example $g \cdot s^{-1} \cdot m^{-2}$. Emission is understood as meaning the source strength, which can be expressed in different units depending on the application, for example in mass per unit time, for example $g \cdot s^{-1}$, in the case of a point source such as emission from an industrial plant, in mass per unit length, for example $g \cdot m^{-1}$, in the case of a line source such as emission from a car, and in mass per unit area per time, for example $g \cdot m^{-2} \cdot s^{-1}$, in the case of a surface source such as methane emission from a bog.

While the method integrates over the whole of the emitted gas mass, like methods 4 and 5 above, it enjoys a number of advantages as compared with these methods:

From the technical point of view, the system is substantially simpler and cheaper than the DIAL system and does not require highly trained personnel for operating it.

Due to the fact that the whole of the spectral interval from UV to IR can be used, it is possible to measure a large number of different molecules with a high degree of specificity.

High light intensity provides low noise level in the measured spectra and consequently a high degree of sensitivity in determining the concentration.

The fact that the measurement is made directly towards the sun, instead of using scattered sunlight from the zenithal sky, results in problems of multiple scattering and the so-called Ring effect being eliminated.

In an alternative application of the method, the instrument is placed stationary in such a way that gas emitted from a mobile source drifts through the (sun—measurement instrument) measurement distance, in conjunction with which the total concentration over a cross section of the gas mass is obtained. After multiplying by the concentration-weighted wind speed perpendicular to the direction of movement of the source, the emission from the source is obtained expressed in mass per unit length, e.g. $g \cdot m^{-1}$. After multiplying by the speed of the source, the emission is obtained expressed in mass per unit time, e.g. $g \cdot s^{-1}$.

The limit of detection and the accuracy when measuring the emission using the proposed method are determined partly by the position in determining the wind field at the heights in question and partly by the precision with which it is possible to determine the integrated concentration. Usually, the wind field is determined by carrying out measurements on the ground, on a mast or with a balloon, after which the total wind field is obtained from interpolation or extrapolation using a meteorological model. An attractive possibility in situations when the wind field is difficult to determine, or when it is difficult to determine the height of the emitted gas, is to use tracer gas in accordance with method 2 above. In this case however, it is necessary for the discharge of the tracer gas to accurately simulate, in time and space, the discharge of the gas under study. This can often be complicated, particularly if the source being studied is extensive, for example a field. An alternative use of tracer gas, and one which is very attractive when measuring with the method which is proposed here, is to directly use the tracer gas for determining the concentration-weighted wind speed. In this application, tracer gas is only released at one or a few points. The concentration-weighted wind speed along the traversing distance is then attained directly with the aid of the measured integrated content of the tracer gas along the traversing distance. The aim of the tracer gas discharge in this present case is consequently to use the integrated content of the tracer gas to obtain the wind speed at the relevant height. If the tracer gas is emitted from an area which is at the same distance from the instrument as is the gas under study, and if the meteorological conditions are similar, this wind speed can then be used when calculating the total emission from the area. In those cases where the distance from the source or the meteorological conditions deviate, the measured concentration-weighted wind speed can be used as a reference value in a model which can subsequently be used to extrapolate to other places or meteorological conditions.

Apart from absorption lines derived from the gas mass under study, the solar spectrum which is measured also contains structures relating to the sun's own spectrum and interfering absorption lines from the total gas composition in the atmosphere. Due to the long absorption distance through the atmosphere, these absorption structures constitute the completely dominant part of the absorption spectrum. When determining the integrated concentration, that which is entirely crucial is how well this background absorption can be eliminated from the spectrum which has been measured. The situation is further complicated by the fact that the sun is moving and, as a result, this background spectrum is changing continuously. Three methods of eliminating this background absorption are described below.

Using the Pure Air Method to Eliminate the Background Absorption

A background spectrum is measured outside of the gas mass which is to be measured. The spectrum which is subsequently measured in the gas mass is then divided by the background spectrum, with the background absorption being eliminated. The method can be improved somewhat by using, as background spectra, the mean value of a spectrum taken before and, respectively, after the measurement. The method works if the background measurement can be made in close conjunction with the emission measurement and preferably in the middle of the day when the height of the sun is close to its maximum and therefore changes slowly.

Use of an Atmosphere Model to Eliminate the Background Absorption

Knowing the vertical composition, pressure and temperature of the atmosphere, it is possible to calculate a synthetic background spectrum for the sun height in question. Measured spectra can then be divided by this background spectrum, with the background absorption being eliminated. The method is complicated and requires access to advanced models and information about the vertical chemical composition and pressure and temperature profile.

Use of the Air Mass Factor to Eliminate the Background Absorption

The third method, which is proposed within the context of the present patent, implies that the background absorption can be eliminated without the observer being located outside of the gas mass under study and without knowledge of the chemical or physical state of the atmosphere. The method is based on it being possible, using what is termed "ray-tracing" algorithm, to calculate, at any given moment, the total optical path length between the instrument and the sun, i.e. what is termed the "air mass factor". Provided that the chemical and physical state of the atmosphere does not change during the measurement, the background absorption will vary in proportion to the variation in the air mass factor. In this connection, it is possible, using multiregression analysis, to calculate which structures in the measured measurement spectra co-vary with the air mass factor and then, since the air mass factor is known for each individual spectrum, eliminate these structures from the individual measured spectra. The method can easily be automated and implemented in real time, does not place any time restriction on the measurements, does not require the recording of "pure" background spectra at regular intervals, and does not demand any knowledge of the chemical composition and physical state of the atmosphere.

According to one embodiment of the method in accordance with the invention, that part of the absorption spectrum which derives from that part of the atmosphere which lies outside of the gas volume under study is calculated by using the variation in the total number of molecules along the optical path between the instrument and the sun, i.e. what is termed the air mass factor, between the different measured spectra is used to determine, by means of correlation analysis the background absorption in each individual spectrum, after which this background absorption is then eliminated from the measured spectrum.

The method in accordance with the present invention is judged to have great potential in many applications. Those which may be mentioned are:

Measuring industrial emissions (petrochemical industry, refineries and forest industry).

Measuring emissions from traffic (cars, boats and aircraft).

Measuring emissions from dumps.

Measuring emissions from activities which cover wide areas, such as agriculture and forestry.

Measuring large-scale emissions from towns, industrial areas and regions.

DESCRIPTION OF THE FIGURES

The invention will be described in more detail below with reference to the implementation examples which are shown on the attached drawings. In this connection.

IMPLEMENTATION EXAMPLES

Figure 1:
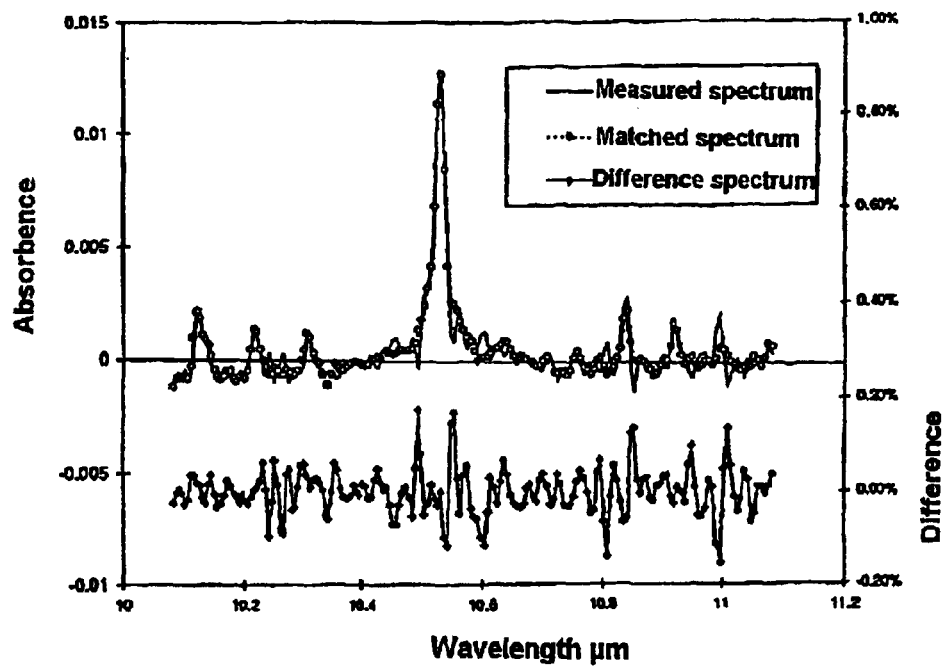
FIG. 1 shows, on the one hand, an absorption spectrum, measured from the solar spectrum, corresponding to 18 ppmm of ethene, which was measured approx. 80 m downwind of a petrochemical plant, and, on the other hand, a scaled reference spectrum of ethene matched to the measured spectrum, and the difference in the matching.

A unique application, for which the method will be used in the very near future, is that of determining the efficiency of flares on petrochemical plants. In connection with certain process disturbances within the petrochemical industry, large quantities of hydrocarbons from different stages in the process are sent to a flare for combustion. The flare is located at the top of a high chimney. The idea is that the hydrocarbons will be burnt in the flare, thereby decreasing the environmental pollution load due to the process disturbance. It is desirable that the efficiency of the combustion in the flare should be high, and this efficiency is usually estimated to be greater than 99%. Ground-based measurement which we have performed using the "long-path FTIR" technique indicate that, in certain cases, the efficiency is considerably less than 99%. An inadequacy in the efficiency of this combustion results in dramatically increased hydrocarbon emissions from the plant and can involve serious consequences, both from the economic point of view (transgressing given licensing conditions) and from the environmental point of view. However, due to the height of the flare above the ground and the high temperature which is reached in the vicinity of the flare during combustion, it is very difficult to measure this efficiency directly. The method which is proposed here offers an unique possibility of measuring the efficiency. This is done by measuring the quantity of gas which is conveyed to the flare by measuring the concentration and flow in the line to the flare. The method which is proposed here is then used to measure the remaining emission of uncombusted hydrocarbons after the flaring by traversing the combustion gas plume from the flare at a suitable distance in the lee of the flare, thereby making it possible to obtain the efficiency. The wind component is determined by adding an inert tracer gas to the gas flow to the flare and then quantifying the tracer gas together with the hydrocarbon emissions in question. In addition to the hydrocarbon emission in question, other gases which are important for understanding and optimizing the course of the combustion, such as CO, $SO_2$ and, where appropriate, $CO_2$, can also be determined at the same time.

The method has been tested in a preliminary manner in several applications. Implementation examples from industrial and agricultural enterprises, respectively, are given below: i.e. measuring emissions of ethene from a petrochemical plant and quantifying the emission of ammonia after spreading manure.

In both cases, what is termed a Bomem MB100 FTIR (Fourier transform infrared) spectrometer, having a spectral resolution of 1 $cm^{-1}$, was used. Spectra were recorded in the infrared region around the 10 $\mu$m wavelength. The sun tracker consisted of a mirror which could be moved in two dimensions (vertically and horizontally, respectively), two fixed mirrors, a lens and what is termed a quadrupole detector. The sunlight impinges on the movable mirror and is directed vertically upwards towards one of the fixed mirrors. In this connection, some of the parallel sunlight is focused by the lens towards the quadrupole detector. The quadrupole detector supplies control signals to the servo motors on the movable mirror and in this way guides in the sunlight so that it is locked onto the centre of the quadrupole detector. The emanating sunlight then has a direction which, by way of the second fixed mirror, is perfectly aligned towards the entry aperture of the spectrometer. As a result of this arrangement, the sunlight will always be directed perfectly towards the spectrometer independently of the movement of the vehicle which is transporting the instrument or of the sun's own movement. The spectra were analysed by means of classical least-squares multiregression analysis after using the air mass factor to eliminate the background absorption. The equipment was placed on the platform of a relatively small truck on a table which was vibration-dampened with air bags.

Figure 2:
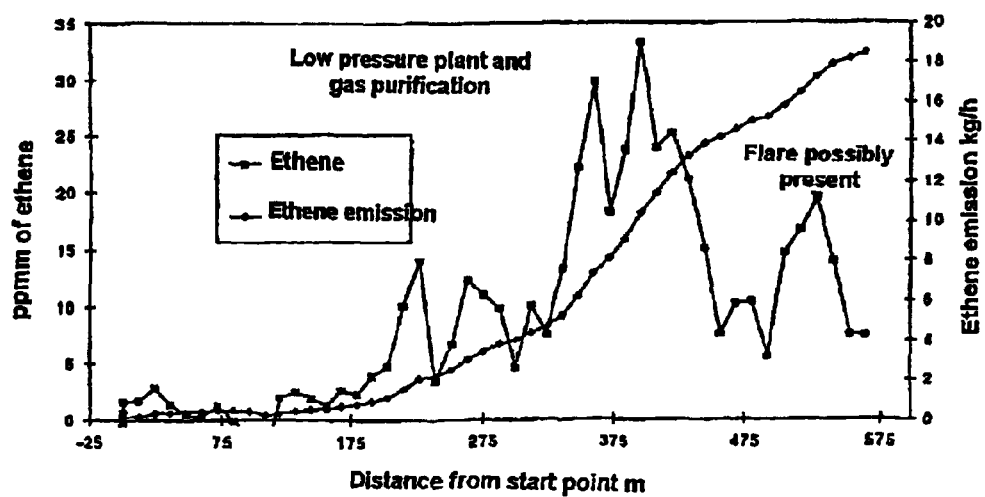
FIG. 2 shows the total column of ethene which was measured approx. 80 m downwind of a petrochemical plant and the integrated emission which was obtained.

Ethene Emission from a Petrochemical Plant:

In this application, the equipment was driven slowly (approx. 1 $m \cdot s^{-1}$) along a path located approx. 80 m on the lee side of a petrochemical plant. FIG. 1 shows an example of a measured spectrum containing 18 ppmm of ethene integrated through the emitted gas mass along the connecting line between the instrument and the sun. The figure also shows a reference spectrum of ethene scaled such that the quadratic deviation between the measured and matched spectrum has been minimized. The difference between the two is also shown as a measure of the quality of the spectral match which was made between the measured spectrum and the reference spectrum. A good match is characterized by the difference spectrum only exhibiting noise randomly and not exhibiting any systematic structures which correlate with the reference spectrum in question. Note that structures down to approx. 0.1% can be measured. FIG. 2 shows the line-integrated ethene concentration, i.e. what is termed the total column, along the instrument-sun line as a function of the location of the measurement vehicle. The figure also shows the integrated emission of ethene, which was calculated using an estimated wind speed and which is summed along the horizontal measurement distance, and the total emission of ethene from the plant was measured to be 18.5 $kg \cdot h^{-1}$. The location of potential discharge sources has been indicated on the figure.

Figure 3:
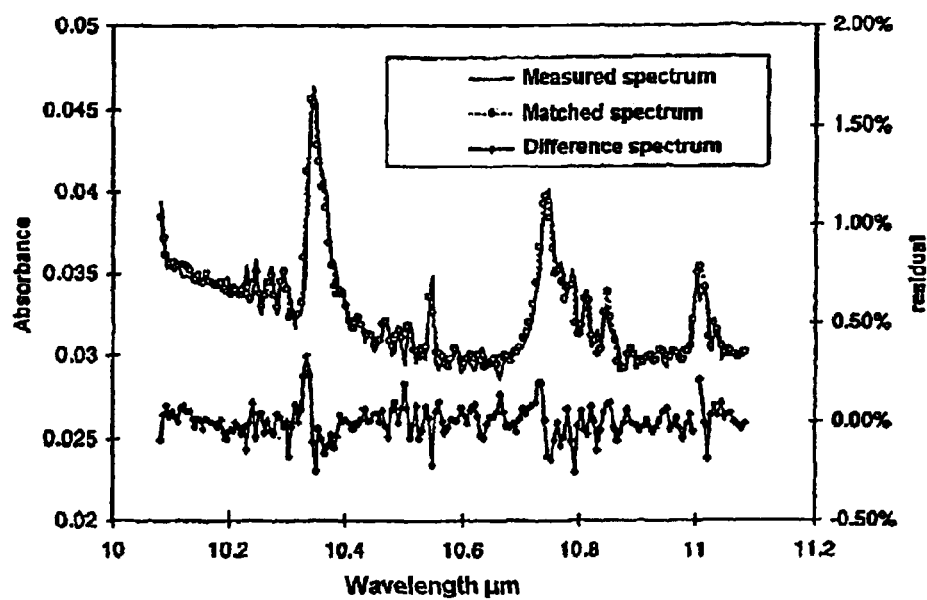
FIG. 3 shows, on the one hand, an absorption spectrum, measured from the solar spectrum, corresponding to 7.8 ppmm of ammonia, which was measured approx. 120 m downwind of a field, of 1.57 ha in size, on which liquid pig slurry had been spread approx. 24 hours earlier, and, on the other hand, a scaled reference spectrum of ammonia matched to the measured spectrum, and the difference in the matching.
Figure 4:
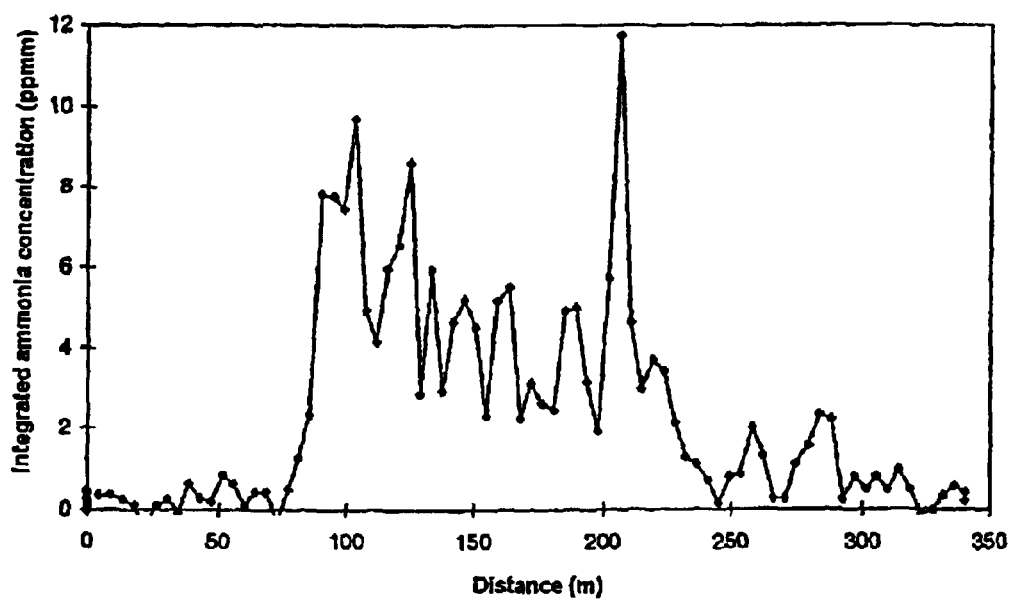
FIG. 4 shows the total column of ammonia ($NH_3$) which was measured approx. 24 hours after fertilizing a field of 1.57 ha in size with pig slurry, with this total column being measured approx. 120 m downwind of the field.

Emission of Ammonia after Spreading Manure:

In this application, the emission of ammonia from a field of 1.57 ha in size was measured 24 hours after spreading pig slurry. The wind direction and the wind speed were measured at a height of 2 meters using a propeller anemometer. The wind direction was at an angle of 77° to the path along which the measurement was carried out, the distance from the field was 120 m and the wind strength was 5.4 $m \cdot s^{-1}$. FIG. 3 shows a spectrum which was measured along the traversal distance, corresponding to an integrated content of 7.8 ppmm. In analogy with FIG. 1, FIG. 3 also shows a matched reference spectrum as well as the difference between the measured and matched spectra. FIG. 4 shows the integrated concentration between the instrument and the sun as a function of the location of the instrument along the traversal distance. The constant contribution made by the background concentration of ammonia in the atmosphere was subtracted, after which the emission of ammonia from the field was measured to be 4.4 kg of $NH_3 \cdot ha^{-1} \cdot h^{-1}$.

What is claimed is:

1. Method for measuring gaseous emissions and/or flux based on using a spectrometer instrument for receiving absorption spectra to detect and record, in a wavelength-resolved manner, the electromagnetic radiation coming directly from the sun, and characterized in that the instrument is arranged in such a way that the connecting line between the instrument and the sun transects a gas volume which constitutes all or a part of the gas flow emitted from a source, in that the recorded electromagnetic radiation is used for calculating the gas concentration along the optical connecting line in the gas volume, and in that the concentration which is obtained in this way, and which is integrated over the cross-sectional area traversed by the connecting line, is used, together with information about the speed of the wind, the instrument and the gas-emitting source, to calculate the gas flow through the cross-sectional area which is traversed.

2. Method according to Patent claim 1, characterized in that the sun is used as the light source and the instrument is transported in such a way that the line which connects the instrument with the sun transects the gas volume which is to be studied, with the totally integrated concentration of the gas under study being determined over the cross-sectional area which is traversed, and in that this quantity is multiplied by the component of the concentration-weighted wind speed over the cross-sectional area which is perpendicular to the direction of transport of the instrument, thereby obtaining the flux of the gas under study through the cross-sectional area which is traversed.

3. Method according to Patent claim 2, characterized in that the concentration-weighted wind field through the traversed gas mass is determined by measuring the concentration, integrated over the cross-sectional area which is traversed, of a tracer gas, which is emitted at a known emission from the area of the source of the gas under study, at the same time as measuring the integrated concentration of the gas under study.

4. Method according to Patent claim 3, characterized in that it is used for locating, identifying and quantifying emissions from industrial plants.

5. Method according to Patent claim 2, characterized in that it is used for locating, identifying and quantifying emissions from industrial plants.

6. Method according to Patent claim 1, characterized in that the sun is used as the light source and the instrument is placed such that the gas volume which is emitted from a movable source is brought by the wind to transect the line which connects the instrument with the sun, with the totally integrated concentration of the gas under study being determined over the cross-sectional area which is traversed, after which this quantity is multiplied by the component of the concentration-weighted wind speed over the cross-sectional area which is perpendicular to the direction of transport of the movable source, resulting in the emission of the gas under study, expressed per unit length as the source moves, being obtained.

7. Method according to Patent claim 6, characterized in that the speed of the source is known, for which reason the emission of the source, expressed per unit of time, can be determined by multiplying the emission of the source per unit length, as the source moves, by the speed of the source.

8. Method according to Patent claim 1, characterized in that that part of the absorption spectrum which is derived from that part of the atmosphere which lies outside of the gas volume under study is calculated by using the variation, between different measured spectra, in the total number of molecules along the optical path between the instrument and the sun, i.e. what is termed the air mass factor, to determine, by means of correlation analysis, the background absorption in each individual spectrum, after which this background absorption is eliminated from the measured spectrum.

9. Method according to Patent claim 8, characterized in that it is used for locating, identifying and quantifying emissions from industrial plants.

10. Method according to Patent claim 1, characterized in that it is used for locating, identifying and quantifying emissions from industrial plants.

* * * * *